United States Patent [19]

Szalay et al.

[11] Patent Number: 5,976,796
[45] Date of Patent: Nov. 2, 1999

[54] CONSTRUCTION AND EXPRESSION OF RENILLA LUCIFERASE AND GREEN FLUORESCENT PROTEIN FUSION GENES

[75] Inventors: Aladar A. Szalay, Highland; Gefu Wang, Redlands; Yubao Wang, Loma Linda, all of Calif.

[73] Assignee: Loma Linda University, Loma Linda, Calif.

[21] Appl. No.: 08/771,850

[22] Filed: Dec. 23, 1996

Related U.S. Application Data

[60] Provisional application No. 60/027,657, Oct. 4, 1996, abandoned.

[51] Int. Cl.⁶ .............................. C12Q 1/66; C12P 21/04; G01N 33/53; C07H 21/04
[52] U.S. Cl. .................... 435/6; 435/8; 435/69.1; 435/69.7; 435/183; 436/548; 530/350; 536/23.4
[58] Field of Search ............................ 435/8, 69.1, 69.7, 435/968, 6, 183; 530/350, 825; 536/23.1, 23.2, 23.4, 23.7; 436/548

[56] References Cited

PUBLICATIONS

Kobatake et al. Bioluminescent immunoassay with a protein A–luciferase fusion protein, Anal. Biochem. 208:300–305, 1993.

Ward et al. An energy transfer protein in Coelenterate bioluminescence, J. Biol. Chem. 254:781–788, 1979.

Mitra et al. Fluorescence resonance energy transfer between blue–emitting and red–shifted excitation derivatives of the green fluorescent protein, Gene 173:13–17, 1996.

Mayerhofer, R. et al., "Expression of recombinant Renilla luciferase in transgenic plants results in high levels of light emission," *The Plant Journal* 7(6): 1031–1038 (1995).

Zolotukhin, S. et al., "A 'Humanized Green' Fluorescent Protein cDNA Adapted for High–Level Expression in Mammalian Cells," *Journal of Virology* 70:4646–4654 (1996).

*Primary Examiner*—Patricia A. Duffy
*Attorney, Agent, or Firm*—David A. Farah; Sheldon & Mak, Inc.

[57] ABSTRACT

A fusion gene is provided comprising the cDNA of Renilla luciferase and the cDNA of the "humanized" Aequorea green fluorescent protein. The fusion gene was used to produce a novel protein, the "Renilla-GFP fusion protein," which displayed both the luciferase activity of Renilla luciferase, and the green fluorescence of GFP. The Renilla-GFP fusion gene is useful as a double marker for monitoring gene expression quantitatively in UV light and by enzyme activity.

5 Claims, 10 Drawing Sheets

FIG. 1

Fusion Gene Cassettes for *E. coli*

Fusion Gene Cassettes for Mammalian cells

CONSTRUCTION AND EXPRESSION OF RENILLA LUCIFERASE AND GREEN FLUORESCENT PROTEIN FUSION GENES

CROSS-REFERENCE TO RELATED APPLICATIONS

The present application is a Continuation-in-Part of the U.S. Provisional Patent Application Ser. No. 60/027,657, filed Oct. 4, 1996 now abandoned entitled "The Construction and Expression of Renilla Luciferase and Green Fluorescent Fusion Genes in *E. coli* and Mammalian Cells," the contents of which are incorporated herein by reference in its entirety.

BACKGROUND

Green Fluorescent Protein (GFP) is a light emitting protein purified from the jellyfish *Aequorea victoria*. GFP can emit green light by accepting energy transfer from sources that include exogenous blue light and Renilla luciferase catalyzed reactions. The gene for GFP was cloned and its cDNA is a powerful reporter gene in a variety of living systems, including bacteria, fungi, and mammalian tissues. The UV light stimulated GFP fluorescence does not require cofactors and the gene product alone can be sufficient to allow detection of living cells under the light microscope.

By modifying the wild type GFP protein, red-shifted GFP variants with bright emission have also been produced. These variants include EGFP, GFPS65T and RSGF. Recently, GFP was expressed in a human cell line and in vivo. C. Kaether, H. H. Gerdes. Visualization of protein transport along the secretory pathway using green fluorescent protein. FEBS-Lett. 1995; 369:267–71. "Humanized" GFP was synthesized with nucleotide changes that did not change the amino acid sequences with one exception.

Renilla luciferase is an enzyme purified from *Renilla reniformis*. The enzyme catalyzes the oxidative decarboxylation of coelenterazine in the presence of oxygen to produce blue light with an emission wavelength maximum of 478 nm. In *Renilla reniformis* cells, however, this reaction is shifted toward the green with a wavelength maximum of 510 nm due to an energy transfer to a Green Fluorescent Protein.

The gene for Renilla luciferase (ruc) was cloned and its cDNA was shown to be useful as a reporter gene in various living systems. D. C. Prasher, V. K. Eckenrode, W. W. Ward, F. G. Prendergast, M. J. Cormier. Primary structure of the *Aequorea victoria* green-fluorescent protein. Gene 1992; 111:229–33. By providing appropriate promoters to the cDNA as gene cassettes, the gene was expressed in bacteria, transformed plant cells, and mammalian cells. The high efficiency of Renilla luciferase is a useful trait as a marker enzyme for gene expression studies.

Given the properties of GFP and Renilla luciferase, it would be useful to have a single protein combining the functions of both Renilla luciferase enzymes and GFP to monitor gene expression quantitatively by UV light excitation or qualitatively by enzyme activity measurements.

SUMMARY

According to one embodiment of the present invention, there are provided fusion gene constructs comprising the cDNA of Renilla luciferase and the cDNA of the "humanized" Aequorea green fluorescent protein. The fusion gene constructs were used to transform both prokaryotic and eukaryotic cells. One construct was expressed as a polypeptide having a molecular weight of about 65 kDa. This polypeptide, the "Renilla-GFP fusion protein," was bifunctional, displaying both the luciferase activity of Renilla luciferase and the green fluorescence of GFP. The Renilla-GFP fusion gene is useful as a double marker for monitoring gene expression in living cells and quantitatively by enzymatic activity.

The invention includes a protein comprising a polypeptide having both luciferase and GFP activities, or biologically active variants of a polypeptide having both luciferase and GFP, or a protein recognized by a monoclonal antibody having affinity to the polypeptide having both luciferase and GFP activities. The polypeptide can be made by recombinant DNA methods.

The invention further includes a high affinity monoclonal antibody that immunoreacts with the polypeptide. The antibody can have an Fc portion selected from the group consisting of the IgM class, the IgG class and the IgA class. The invention also includes a high affinity monoclonal antibody that immunoreacts with a polypeptide having both luciferase and GFP activities.

The invention further includes a polynucleotide sequence coding for a polypeptide having both luciferase and GFP activities, or its complementary strands, and a polynucleotide sequence that hybridizes to such a sequence and that codes on expression for a polypeptide having both luciferase and GFP activities, or its complementary strands.

The invention further includes a purified and isolated DNA molecule comprising a polynucleotide coding for a polypeptide having both luciferase and GFP activities, or its complementary strands. The polynucleotide can comprise the sequence as set forth in SEQ ID NO:1.

The invention further includes a vector containing a DNA molecule coding for a polypeptide having both luciferase and GFP activities. The polynucleotide can comprise the sequence as set forth in SEQ ID NO:1. The vector can be used to stably transform or transiently transfect a host cell.

The invention further includes a method of making a polypeptide having both luciferase and GFP activities. The method comprises the steps of, first, culturing a microorganism transformed with a polynucleotide vector containing a gene cassette coding for a polypeptide having both luciferase and GFP activities. Next, the polypeptide having both luciferase and GFP activities is recovered.

The invention further includes a method of quantifying promoter activations and GFP fluorescence based on luciferase activity measurements. The method comprises the step of providing the polypeptide according to the present invention.

The invention further includes a method of making a monoclonal antibody that immunoreacts with a polypeptide having both luciferase and GFP activities. The method comprises the steps of, first, administering to a host a polypeptide having both luciferase and GFP activities in an amount sufficient to induce the production of antibodies to the polypeptide from the host's antibody-producing cells. Next, the antibody-producing cells are recovered from the host. Then, cell hybrids are formed by fusing the antibody-producing cell to cells capable of substantially unlimited reproduction. Then, the hybrids are cultured. Next, the monoclonal antibodies are collected as a product of the hybrids.

The invention further includes a method of monitoring gene expression quantitatively and qualitatively in a cell using a gene fusion construct coding for a polypeptide having both luciferase and GFP activities. The method comprises the steps of, first, providing a gene fusion construct coding for a polypeptide having both Renilla luciferase and GFP activity. Next, the gene fusion construct is introduced into the cell. Then, the cell containing the gene fusion construct is maintained in a manner allowing the cell to express the polypeptide. Then, the cell is measured for luciferase and fluorescent activity. The construct can include a polynucleotide sequence as set forth in SEQ ID NO:1.

The invention further includes a method of monitoring gene expression quantitatively and qualitatively in a cell using a gene fusion construct coding for a polypeptide having both luciferase and GFP activities. The method comprises the steps of, first, providing a gene fusion construct coding for a polypeptide having both luciferase and GFP activities. Next, the gene fusion construct is introduced into the cell. Then, the cell containing the gene fusion construct is maintained in a manner allowing the cell to express the polypeptide. Next, the cell is measured for luciferase and fluorescent activity.

FIGURES

These and other features, aspects and advantages of the present invention will become better understood with regard to the following description, appended claims, and accompanying figures where:

DESCRIPTION

According to one embodiment of the present invention, there is provided a fusion gene comprising the cDNA of Renilla luciferase and the cDNA of the "humanized" Aequorea green fluorescent protein. According to another embodiment of the present invention, there is provided a single polypeptide that exhibits both Renilla luciferase and GFP activities. This bifunctional polypeptide can facilitate the identification of transformed cells at the single cell level, in cell cultures, transformed tissues and organs based on fluorescence of the polypeptide. At the same time, the polypeptide can also be used to quantify promoter activations and GFP fluorescence based on luciferase activity measurements. The cDNA of *Renilla reniformis* luciferase (ruc) has been cloned and used successfully as a marker gene in a variety of transgenic species. See, for example, Lorenz, W. W. McCann, R. O., Longiaru, M. and Cormier, M. J. Isolation and expression of a cDNA encoding *Renilla reniformis* luciferase. Proc. Natl. Acad. Sci. USA 1991; 88:4438–4442; Mayerhofer, R., Langridge, W. H. R., Cormier, M. J., and Szalay, A. A. Expression of recombinant Renilla luciferase in transgenic plants results in high levels of light emission. The Plant Journal 1995; 7:1031–1038; and Lorenz, W. W., Cormier, M. J., O'Kane, D. J., Hua, D., Escher, A. A. Szalay, A. A. Expression of the *Renilla reniformis* luciferase gene in mammalian cells. J. Biolumin. Chemilumin. 1995; 11:31–37, incorporated herein by reference in their entirety. Similarly, the transfer and expression of Green-Fluorescent-Protein (GFP) cDNA from *Aequorea victoria* resulted in high levels of GFP in transformed cells that allowed convenient visualization of individual cells under the microscope. See, for example, Chalfie, M., Tu, Y., Euskirchen, G., Ward, W. W. and Prasher, D. C. Green fluorescent protein as a marker for gene expression. Science 1994; 263:802–805, incorporated herein by reference in its entirety.

The present invention involves the production of fusion genes from the cDNA of Renilla (ruc) and the cDNA of the "humanized" Aequorea GFP ($gfp_h$). A description of "humanized" Aequorea GFP ($gfp_h$) can be found, for example, in Zolotukhin, S., Potter, M., and Huaswirth, W. W., Guy, J., and Muzyczka, N. A "humanized" green fluorescent protein cDNA adapted for high-level expression in mammalian cells. J. Virology 1996; 70:4646–4654, incorporated herein by reference in its entirety.

Figure 1:
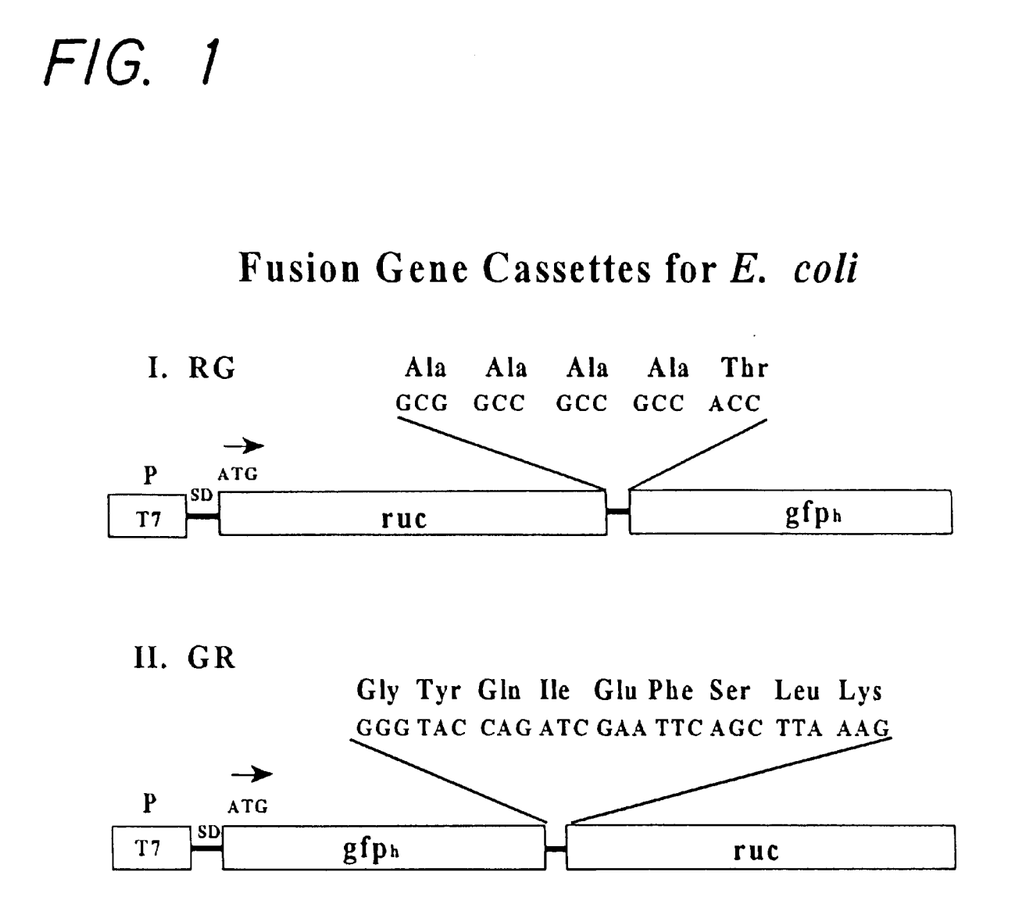
FIG. 1 is a schematic diagram showing the construction of a Renilla luciferase and "humanized" GFP fusion gene cassette according to the present invention for gene expression in E. coli where "RG," top, is the fusion gene cassette with the Renilla luciferase coding sequence (ruc) at the 5' terminus, and "GR," bottom, is the fusion gene cassette with the GFP coding sequence ($gfp_h$) at the 5' terminus.
Figure 2:
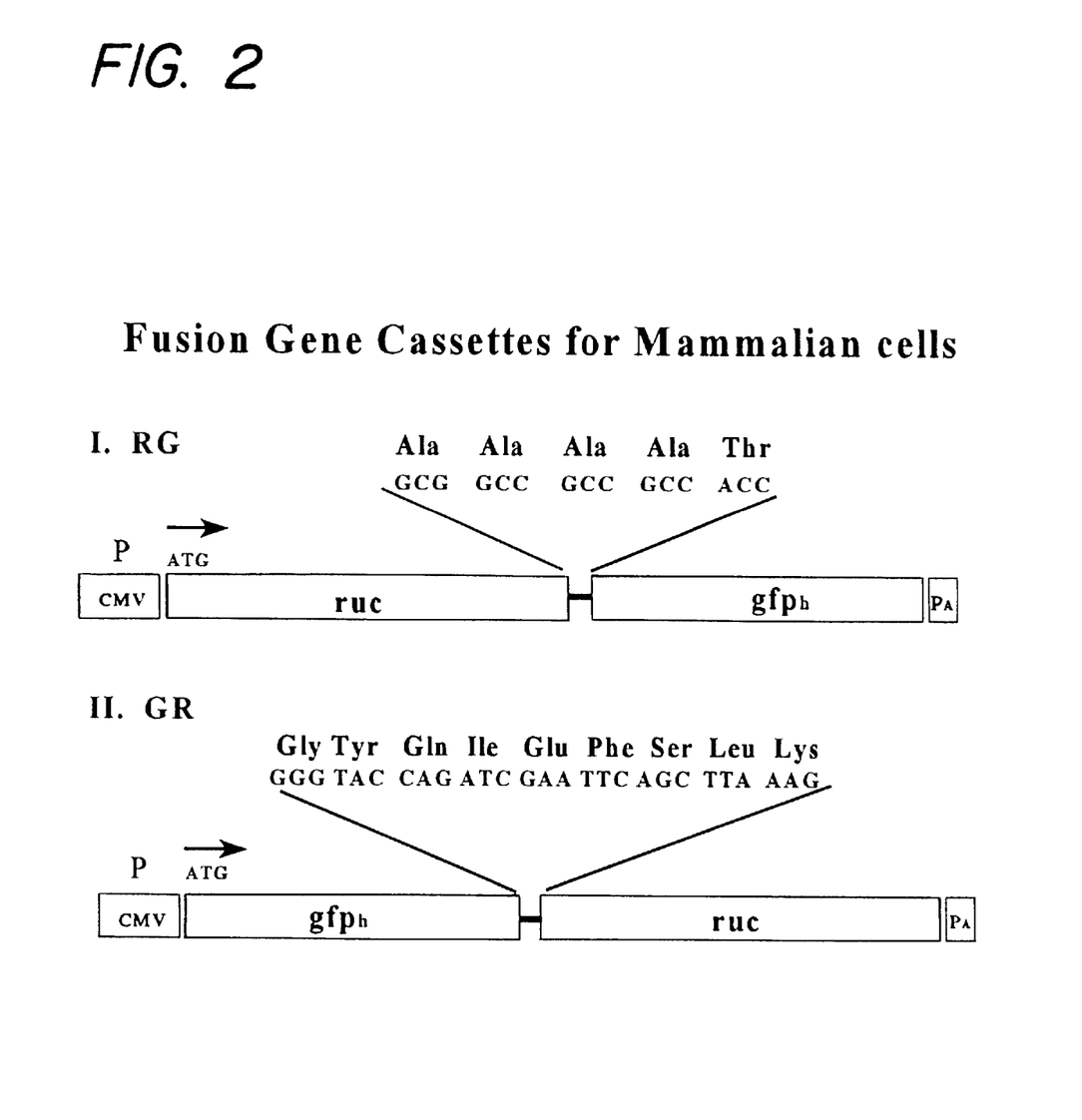
FIG. 2 is a schematic diagram showing the construction of Renilla luciferase and "humanized" GFP fusion gene cassette according to the present invention for gene expression in mammalian cells where "RG," top, is the fusion gene cassette with the Renilla luciferase coding sequence (ruc) at the 5' terminus, and "GR," bottom, is the fusion gene cassette with the GFP coding sequence ($gfp_h$) at the 5' terminus.

The first fusion gene, designated the "RG fusion gene," SEQ ID NO:1 and shown at the top of FIGS. 1 and 2, contains the Renilla cDNA linked at the modified 3' end to a fifteen polynucleotide linker sequence encoding five amino acids, Ala-Ala-Ala-Ala-Thr, residues 312–316 of SEQ ID NO:1, followed by the 5' end of the intact GFP cDNA. The second fusion gene, designated the "GR fusion gene," SEQ ID NO:2 and shown at the bottom of FIGS. 1 and 2, contains the cDNA of GFP linked to a twenty-seven polynucleotide linker sequence encoding nine amino acids, Gly-Try-Gln-Ile-Glu-Phe-Ser-Leu-Lys, residues 239–247 of SEQ ID NO:2, followed by the 5' end of Renilla cDNA. Both genes were placed into prokaryotic pGEM-5zf(+) and eukaryotic pCEP4 expression vectors, and transformed into E. coli, and various mammalian cell lines, and microinjected into mouse embryos. $PT_7$ was the bacterial T7 promoter used for gene expression. $P_{cmv}$ was the CMV promoter used for gene expression in mouse fibroblast cells, embryonic stem cells and mouse embryos.

Unexpectedly, only cells transformed with the RG fusion gene gave strong fluorescence while the cells containing the GR fusion gene exhibited minimal response to UV light under the microscope. In contrast, luciferase measurements in homogenates of cells transformed with RG gene cassettes or with GR gene cassettes were indistinguishable from each other in both bacterial and mammalian cells. Further, spectrofluorimeter data indicated that there was energy transfer between Renilla luciferase and GFP in the RG fusion gene containing cells but did not indicate such energy transfer in cells containing the GR fusion gene. The protein expressed in the RG fusion gene containing cells was analyzed and found to be a 65 kDa polypeptide. A detailed description of the construction and expression of the fusion genes, and analyses of their protein products is given below.

Figure 3A:
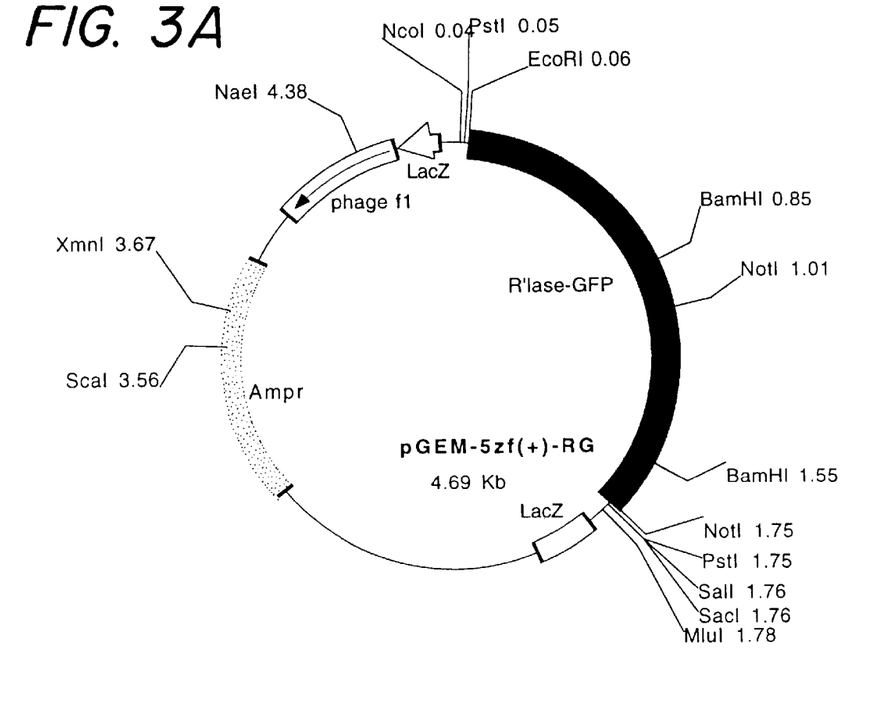
FIG. 3 is a map of the plasmids used for cloning and expression of the RG gene construct in E. coli (top) and the GR gene construct in E. coli (bottom)
Figure 3B:
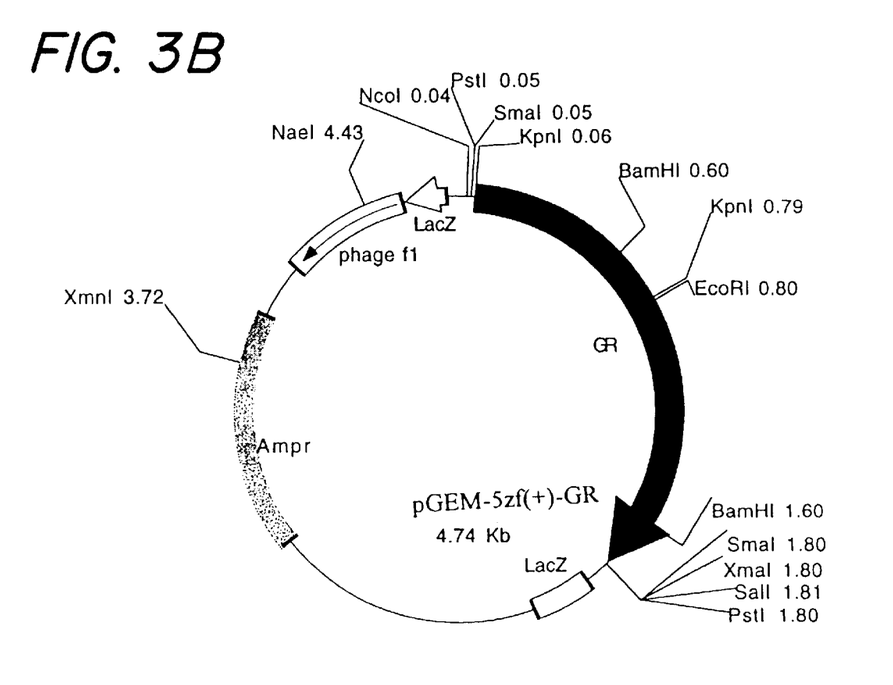

Production of the Fusion Gene Constructs:

The vectors used for cloning and expression of the gene constructs in E. coli and mammalian systems were pGEM-5zf(+) (Promega) and pCEP4, respectively. FIG. 3 is a map of the plasmids used for cloning and expression of the RG gene construct in E. coli, pGEM-5zf(+)-RG (top) and the map of the plasmids used for cloning and expression of the GR gene construct in E. coli, pGEM-5zf(+)-GR (bottom). Both were under the transcriptional control of T7 promoter. The E. coli strains which were transformed were DLT101 and DH5α.

Figure 4A:
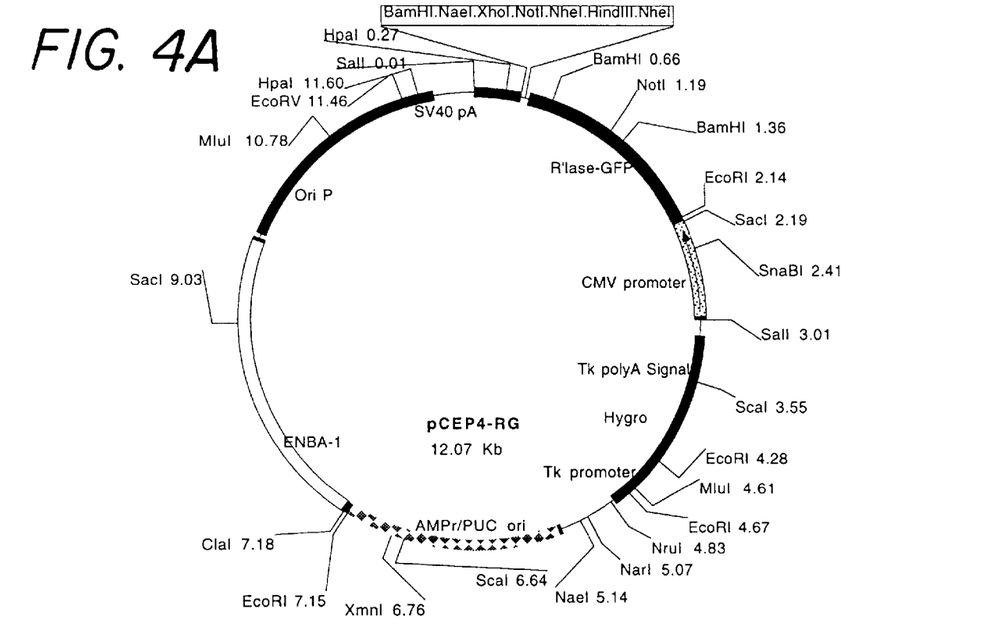
FIG. 4 is a map of the plasmids used for cloning and expression of the RG gene construct in mammalian systems (top) and the GR gene construct in mammalian systems (bottom)
Figure 4B:
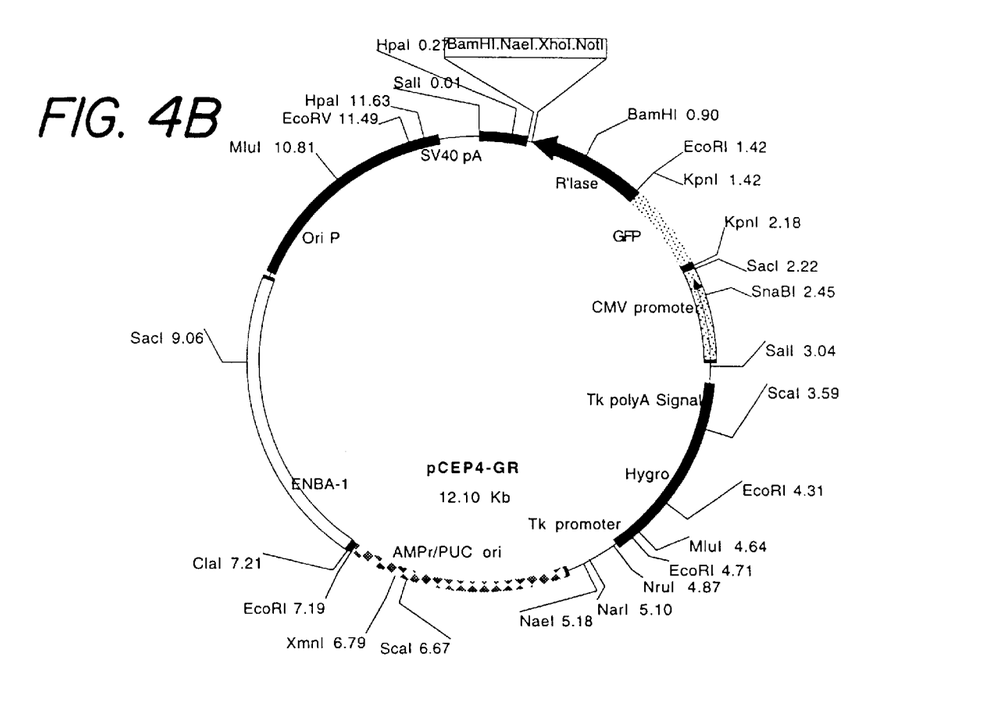

Similarly, FIG. 4 is a map of the plasmids used for cloning and expression of the RG gene construct in mammalian systems, pCEP4-RG (top), and a map of the plasmids used for cloning and expression of the GR gene construct in mammalian systems, pCEP4-GR (bottom). Both were under the transcriptional control of CMV promoter. The mammalian cell line that was transformed was LM-TK⁻ embryonic stem cells and embryos.

Five primers were designed for cloning the RG and GR gene constructs. Single underlines indicate Shine-Dalgarno sequences. Double underlines indicate the restriction sites. The start codons are in bold. Sequences in bold italics indicate the removal of stop codons from both ruc and gfp$_h$ genes.

Primer 1, SEQ ID NO:3: RUC5: 5'CTGCAG (PstI) AGGAGGAATTCAGCTTAAAGATG3'

Primer 2, SEQ ID NO:4: RUC3: 5'GCGGCCGC (Not I) TTG TTCATTTTTGAGAAC3'

Primer 3, SEQ ID NO:5: GFP5:5'GGGGTACC (KpnI) CCATGAGCAAGGGCGAGGAACT3'

Primer 4, SEQ ID NO:6: GFP3: 5'GGGGTACC (KpnI) CCTTGTACAGCTCGTCCATGCCA3'

Primer 5, SEQ ID NO:7: GFP5a 5'CCCGGG (SmaI) AGGAGGTACCCCATGAGCAAG3'.

The Renilla luciferase-GFP fusion gene (RG gene cassette) and the GFP-Renilla luciferase fusion gene (GR gene cassette) were constructed by removing the stop codons, and by adding restriction sites and Shine-Dalgarno sequences to the 5' end of the cDNAs using PCR according to techniques known to those with skill in the art. The PCR products were cloned using the pGEM-T system (Promega Corporation, Madison, Wis.). Primers were designed so that the downstream cDNA is in frame with the upstream cDNA. The linker sequences are shown in FIGS. 1 and 2 and described above. After cloning, the RG and GR gene cassettes were under the transcriptional control of T7 in pGEM-5zf(+) vector and CMV in pCEP4 vector, which were used for expression in E. coli and mammalian cells, respectively.

Determination of Activity of Fusion Genes and Their Corresponding Protein Products:

GFP activity in vivo was visualized as follows. E. coli strain DH5α was transformed with the plasmids pGEM-5zf(+)-RG and pGEM-5zf(+)-GR. Positive colonies were identified and cultured in LB medium with 100 μg/ml of ampicillin selection, according to techniques known to those with skill in the art. Twelve hours later, one drop of E. coli culture was put on a slide and visualized by fluorescent microscopy at 1000×magnification. LM-TK⁻ cells were transfected with plasmids pCEP4-RG and pCEP4-GR using calcium phosphate methods known to those with skill in the art. The culture dishes were monitored using an inverted fluorescent microscope 12 hours after the transfection.

Luciferase activity was assayed as follows. An aliquot of transformed E. coli was used for a luciferase assay in a Turner TD 20e luminometer (Turner Designs, Sunnyvale, Calif.), both before and after IPTG induction. The results were recorded as relative light units. Mammalian cells harvested 36 hrs after transfection were measured for luciferase activity.

Corrected emission spectra were detected spectrofluorimetrically using a SPEX fluorolog spectrofluorimeter operated in the ratio mode. Fluorescence emission was excited at 390 nm. Bioluminescence emission was recorded with the excitation beam blocked following the addition of 0.1 μg of coelenterazine in acidified methanol. Five spectra were averaged for each sample over a wavelength range from 400 to 600 nm.

The fusion proteins were isolated and immunoactivity detected as follows. 1 ml of E. coli ($OD_{600}$=1.0) was harvested. 400 μl of cell suspension buffer (0.1M NaCl, 0.01 M Tris—HCl pH 7.6, 0.001 M EDTA, 100 μg/ml PMSF) and 100 μl of loading buffer (50 mM Tris—HCl pH 6.8, 2% SDS, 10% glycerol, 5% 2-mercaptoethanol) were added. The samples were boiled for 4 min and loaded to a 7.5%–20% gradient SDS-polyacrylamide gel. Polyclonal anti-Renilla luciferase was used as the primary antibody for detection and goat peroxidase anti-IgG (anti-rabbit) as the secondary antibody.

Figure 5A:
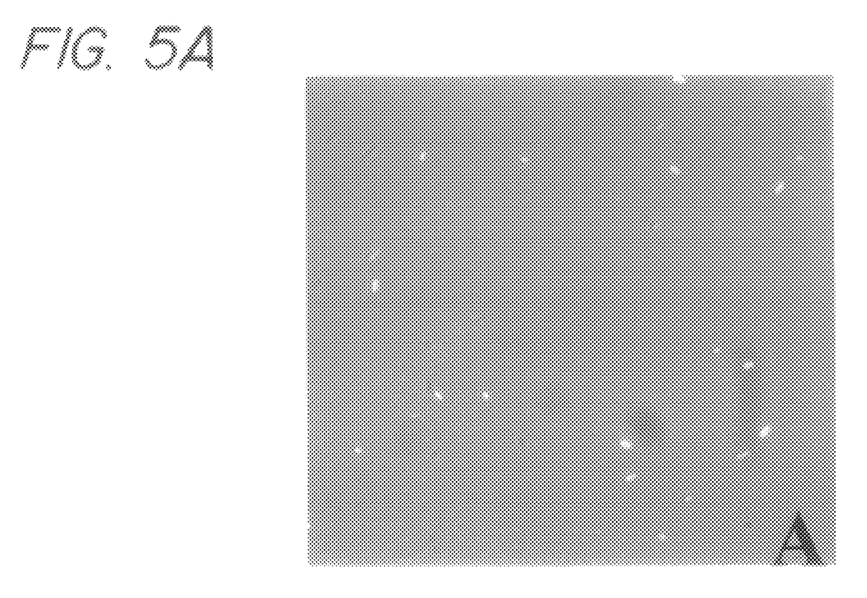
FIGS. 5A and 5B are photomicrographs of cells transformed by the fusion genes using fluorescence microscopy and fluorescence imaging to show GFP activity.
Figure 5B:
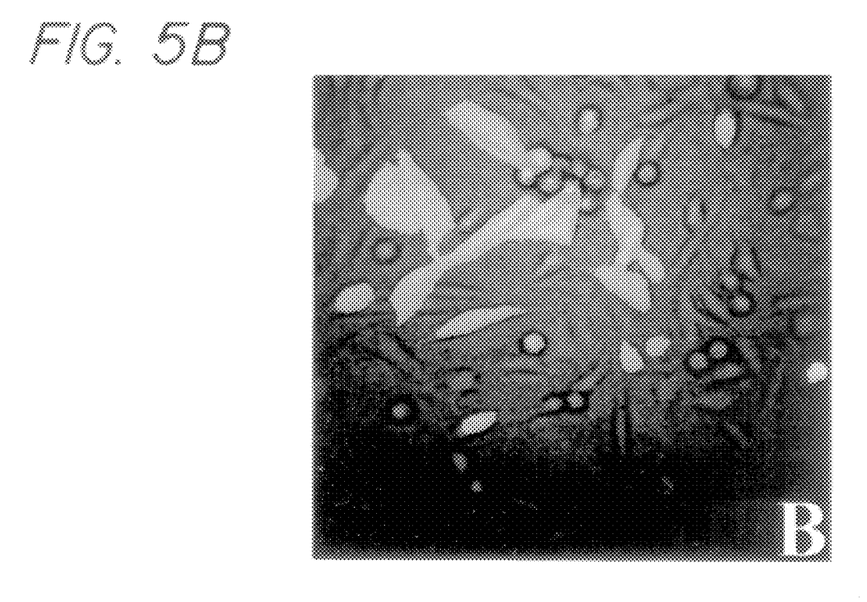

Referring now to FIGS. 5A and 5B, there are shown photomicrographs of GFP activity in transformed E. coli cells (5A, left side) and LM-TK⁻ mouse fibroblast cells (5B, right side) by fluorescence microscopy and fluorescence imaging. As can be seen, individual E. coli cells and mammalian cells transformed with the RG fusion gene construct exhibited strong green fluorescence under oil immersion.

Figure 6A:
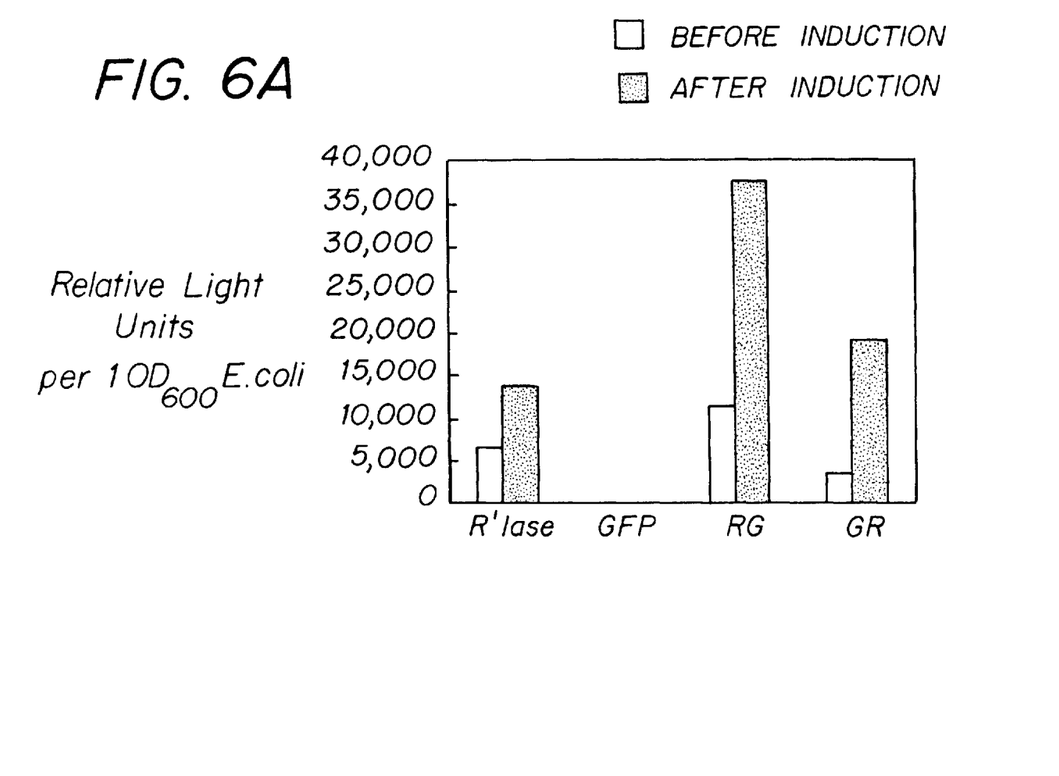
FIGS. 6A and 6B are bar graphs of luciferase activity of the fusion gene constructs in E. coli (top) and mammalian cells (bottom)
Figure 6B:
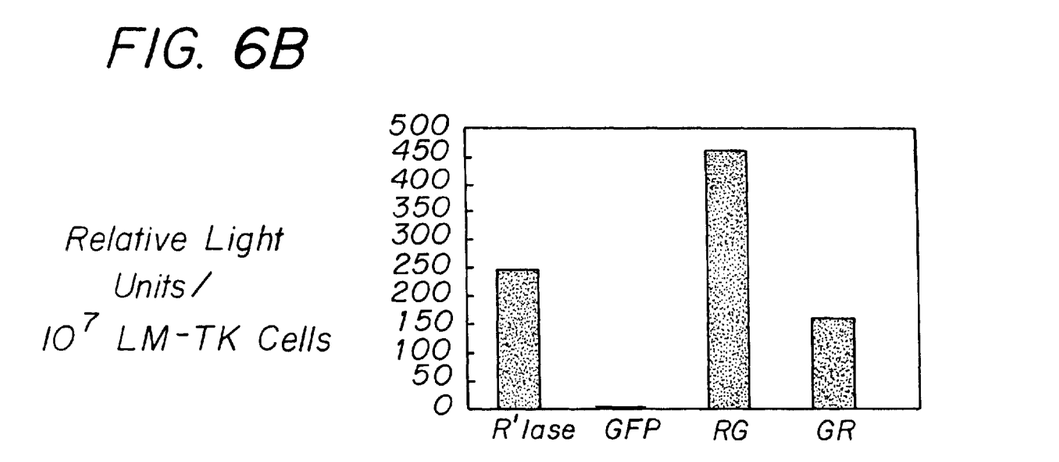

Referring now to FIGS. 6A and 6B, there are shown bar graphs of luciferase activity of the gene constructs in E. coli, FIG. 6A and mammalian cells, FIG. 6B. The white bars indicate activity before promoter induction. The black bars indicate activity after promoter induction. As can be seen, cells transformed with the RG fusion gene construct have significant luciferase activity, which is reduced 3-fold in the cells transformed with the GR fusion gene construct.

Figure 7:
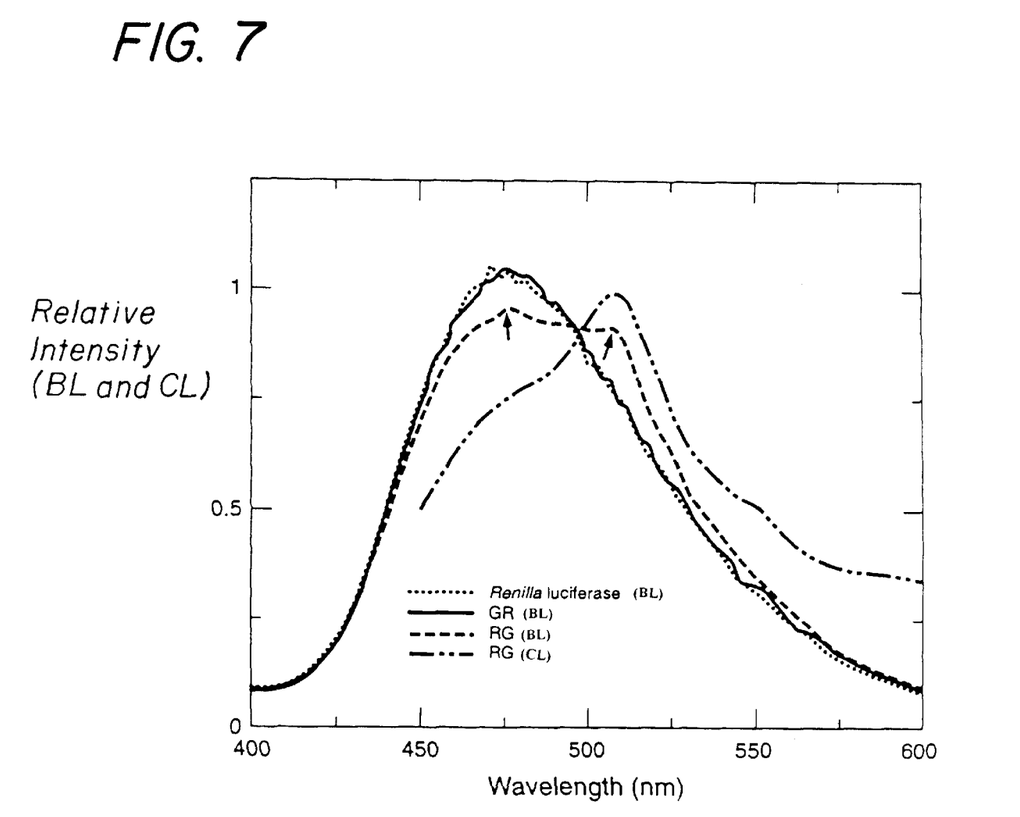
FIG. 7 is a spectroscopic measurement of Renilla luciferase activity and GFP activity in E. coli.

Referring now to FIG. 7, there is shown a spectroscopic measurement of Renilla luciferase activity and GFP activity in E. coli transformed with various gene constructs. As can be seen, cells containing Renilla luciferase gene (short dashes) show only one emission peak at approximately 478 nm. Cells containing the GR gene fusion construct (light solid) also show one emission peak at approximately 478 nm, indicating Renilla luciferase activity only. By contrast, cells containing the RG gene fusion construct (heavy solid) show an emission peak at approximately 510 nm with excitation at 390 nm. Cells containing the RG gene fusion construct with the addition of coelanterizine (long dashes) show emission peaks at both approximately 478 nm and 510 nm indicating that the energy transfer between Renilla luciferase and GFP occurred in these cells. The lack of GFP activity in GR gene cassette transformed cell lines could be due to incorrect folding, due to the requirement for a free GFP C-terminus, or due to interference of the linker polypeptide with GFP activity in the fusion protein, among other possible explanations.

Figure 8:
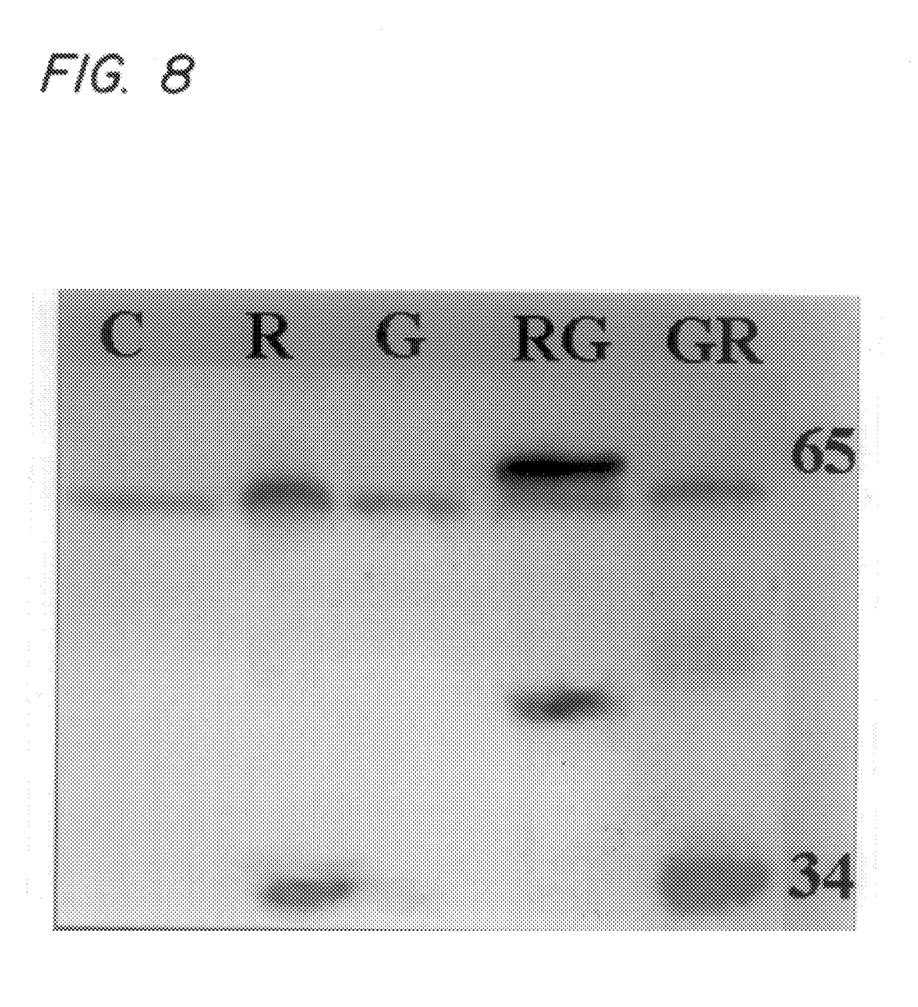
FIG. 8 is a Western blot showing the detection of fusion gene expression in E. coli using anti-Renilla luciferase antibody.
Figure 9A:
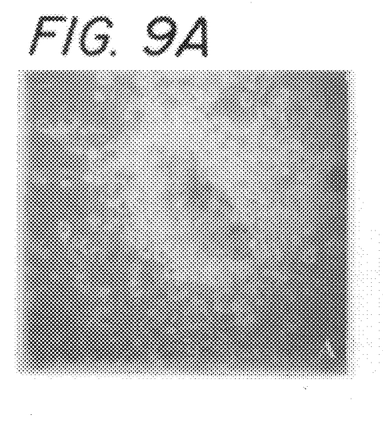
FIGS. 9A through 9F are photomicrographs of mouse embryonic stem cells using fluorescence image analysis demonstrating the expression of the RG fusion gene.
Figure 9B:
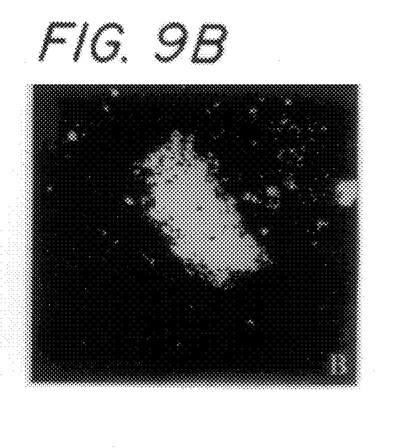
Figure 9C:
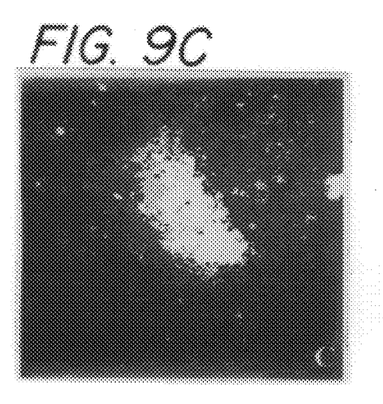
Figure 9D:
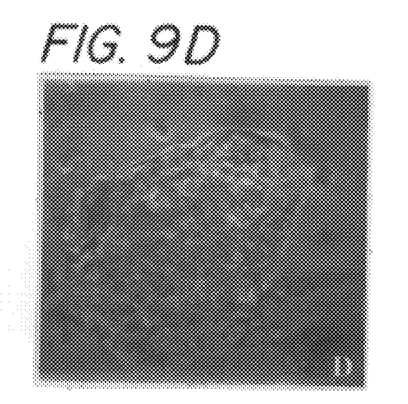
Figure 9E:
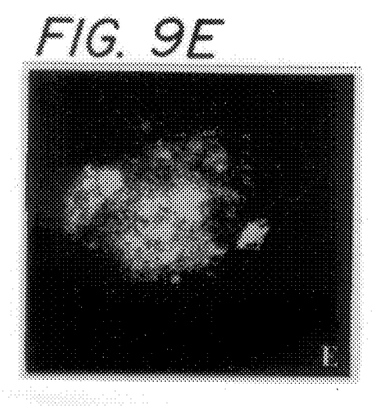
Figure 9F:
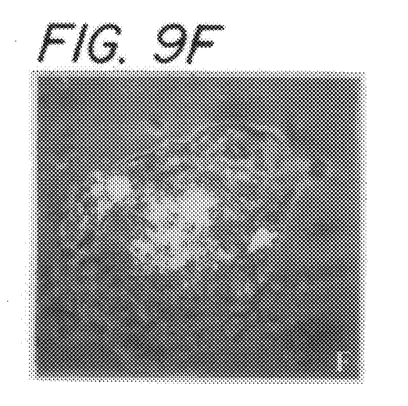

Referring now to FIG. 8, there is shown a western blot used to detect fusion gene expression in E. coli using anti-Renilla luciferase antibody. Reading from left to right, the "C" lane shows the total protein extracted from non-transformed E. coli cells. The "R" lane shows the total protein extracted from E. coli cells transformed with the ruc gene alone. The "G" lane shows the total protein extracted from E. coli cells transformed with the gfp$_h$ gene alone. The "RG" lane shows the total protein extracted from E. coli cells transformed with the RG fusion gene cassette. The "GR" lane shows the total protein extracted from E. coli cells transformed with the GR fusion gene cassette.

As can be seen, protein extracted from E. coli cells transformed with the ruc gene alone produced a band with a molecular weight of about 34 kDa. Protein extracted from E. coli cells transformed with the RG fusion gene cassette produced a band with a molecular weight of about 65 kDa. Protein extracted from E. coli cells transformed with the GR fusion gene cassette produced a band with a molecular weight of about 34 kDa. These data imply that cells transformed with the GR fusion gene cassette produced luciferase but did not produce fusion protein. Such a lack of fusion protein production by cells transformed with the GR fusion cassette would explain the lack of green fluorescent activity in these cells.

Referring now to FIGS. 9A through 9F, there are shown photomicrographs using fluorescence image analysis demonstrating the expression of the RG fusion gene in mouse embryonic stem cells transformed by electroporation procedures. Transformed colonies were selected based on GFP activity under fluorescence microscopy.

Figure 10A:
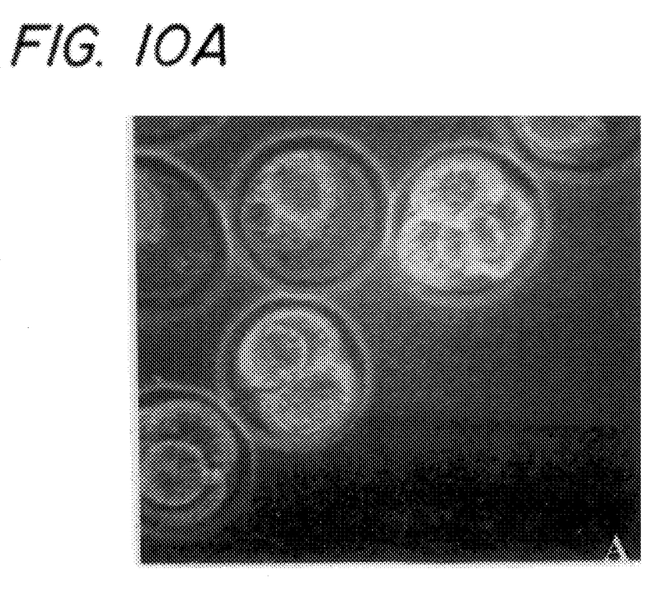
FIGS. 10A and 10B are photomicrographs of mouse embryos using fluorescence image analysis demonstrating the expression of the RG fusion gene.
Figure 10B:
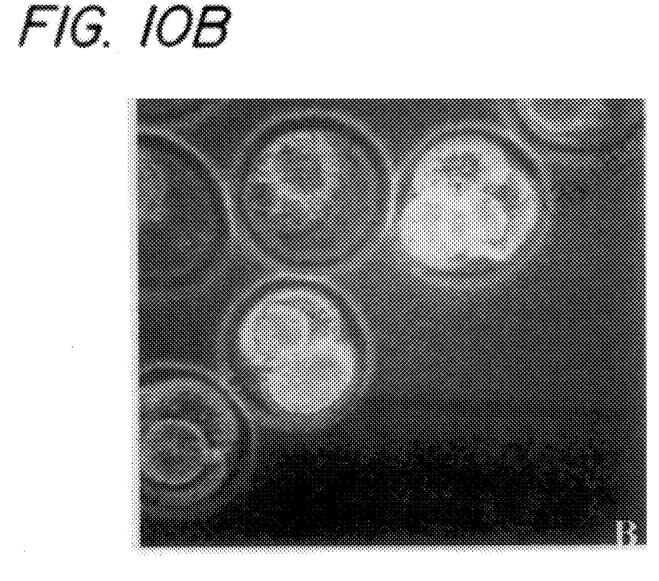

Referring now to FIGS. 10A and 10B, there are shown photomicrographs using fluorescence image analysis demonstrating the expression of the RG fusion genes in mouse embryos. The embryos were injected with the linearized RG plasmid, and in vitro cultured. The expression of GFP activity was monitored daily by fluorescent microscope and recorded by an imaging collection system.

Based on this data, we conclude that the RG fusion construct disclosed herein can be expressed in both prokaryotic and eukaryotic cells to produce a bifunctional polypeptide that exhibits both Renilla luciferase and GFP activity. This bifunctional polypeptide is a useful tool for identification of transformed cells at the single cell level based on fluorescence. It allows the simultaneous quantification of promoter activation in transformed tissues and transgenic organisms by measuring luciferase activity. The dual function of this protein allows the monitoring of bacterial cells in their living hosts and the differentiation of cells in the developing embryo and throughout the entire animal.

Although the present invention has been discussed in considerable detail with reference to certain preferred embodiments, other embodiments are possible. Therefore, the spirit and scope of the appended claims should not be limited to the description of preferred embodiments contained herein.

We claim:

1. A protein comprising an amino acid sequence encoded by the nucleic acid sequence as set forth in SEQ ID NO:1.

2. The protein of claim 1 in purified and isolated form.

3. An improved method of quantifying promotor activation based on green fluorescent protein fluorescence and luciferase activity measurements, wherein the improvement comprises providing an isolated protein comprising an amino acid sequence encoded by the nucleic acid sequence as set forth in SEQ ID NO:1.

4. A method of producing a protein comprising an amino acid sequence encoded by the nucleic acid sequence as set forth in SEQ ID NO:1 comprising:

(a) culturing a microorganism transformed with a vector comprising SEQ ID NO:1 under conditions sufficient to produce the protein; and     (b) recovering the protein.

5. A method of making a monoclonal antibody, the method comprising:

(a) administering to a host, a protein comprising an amino acid sequence encoded by the nucleic acid sequence as set forth in SEQ ID NO:1 in an amount sufficient to induce the production of antibodies to the protein;

(b) recovering the antibody-producing cells from the host;

(c) forming cell hybrids by fusing the antibody-producing cell to cells capable of unlimited reproduction;

(d) culturing the hybrids; and

(e) collecting the monoclonal antibodies as a product of the hybrids.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 1665 base pairs
      (B) TYPE: nucleic acid
      (C) STRANDEDNESS: single
      (D) TOPOLOGY: linear    (xi) SEQUENCE DESCRIPTION: SEQ ID NO:1:

```
ATG ACT TCG AAA GTT TAT GAT CCA GAA CAA AGG AAA CGG ATG ATA ACT        48
Met Thr Ser Lys Val Tyr Asp Pro Glu Gln Arg Lys Arg Met Ile Thr
  1               5                  10                  15

GGT CCG CAG TGG TGG GCC AGA TGT AAA CAA ATG AAT GTT CTT GAT TCA        96
Gly Pro Gln Trp Trp Ala Arg Cys Lys Gln Met Asn Val Leu Asp Ser
             20                  25                  30

TTT ATT AAT TAT TAT GAT TCA GAA AAA CAT GCA GAA AAT GCT GTT ATT       144
Phe Ile Asn Tyr Tyr Asp Ser Glu Lys His Ala Glu Asn Ala Val Ile
         35                  40                  45

TTT TTA CAT GGT AAC GCG GCC TCT TCT TAT TTA TGG CGA CAT GTT GTG       192
Phe Leu His Gly Asn Ala Ala Ser Ser Tyr Leu Trp Arg His Val Val
     50                  55                  60

CCA CAT ATT GAG CCA GTA GCG CGG TGT ATT ATA CCA GAT CTT ATT GGT       240
Pro His Ile Glu Pro Val Ala Arg Cys Ile Ile Pro Asp Leu Ile Gly
 65                  70                  75                  80

ATG GGC AAA TCA GGC AAA TCT GGT AAT GGT TCT TAT AGG TTA CTT GAT       288
Met Gly Lys Ser Gly Lys Ser Gly Asn Gly Ser Tyr Arg Leu Leu Asp
                 85                  90                  95
```

-continued

| | | | | | | | | | | | | | | | |
|---|---|---|---|---|---|---|---|---|---|---|---|---|---|---|---|
| CAT | TAC | AAA | TAT | CTT | ACT | GCA | TGG | TTT | GAA | CTT | CTT | AAT | TTA | CCA | AAG | 336 |
| His | Tyr | Lys | Tyr | Leu | Thr | Ala | Trp | Phe | Glu | Leu | Leu | Asn | Leu | Pro | Lys |
| | | | 100 | | | | | 105 | | | | | 110 | | |

```
CAT TAC AAA TAT CTT ACT GCA TGG TTT GAA CTT CTT AAT TTA CCA AAG        336
His Tyr Lys Tyr Leu Thr Ala Trp Phe Glu Leu Leu Asn Leu Pro Lys
            100                 105                 110

AAG ATC AAT TTT GTC GGC CAT GAT TGG GGT GCT TGT TTG GCA TTT CAT        384
Lys Ile Asn Phe Val Gly His Asp Trp Gly Ala Cys Leu Ala Phe His
            115                 120                 125

TAT AGC TAT GAG CAT CAA GAT AAG ATC AAA GCA ATA GTT CAC GCT GAA        432
Tyr Ser Tyr Glu His Gln Asp Lys Ile Lys Ala Ile Val His Ala Glu
130             135                 140

AGT GTA GTA GAT GTG ATT GAA TCA TGG GAT GAA TGG CCT GAT ATT GAA        480
Ser Val Val Asp Val Ile Glu Ser Trp Asp Glu Trp Pro Asp Ile Glu
145             150                 155                 160

GAA GAT ATT GCG TTG ATC AAA TCT GAA GAA GGA GAA AAA ATG GTT TTG        528
Glu Asp Ile Ala Leu Ile Lys Ser Glu Glu Gly Glu Lys Met Val Leu
                165                 170                 175

GAG AAT AAC TTC TTC GTG GAA ACC ATG TTG CCA TCA AAA ATC ATG AGA        576
Glu Asn Asn Phe Phe Val Glu Thr Met Leu Pro Ser Lys Ile Met Arg
                180                 185                 190

AAG TTA GAA CCA GAA GAA TTT GCA GCA TAT CTT GAA CCA TTC AAA GAG        624
Lys Leu Glu Pro Glu Glu Phe Ala Ala Tyr Leu Glu Pro Phe Lys Glu
            195                 200                 205

AAA GGT GAA GTT CGT CGT CCA ACA TTA TCA TGG CCT CGT GAA ATC CCG        672
Lys Gly Glu Val Arg Arg Pro Thr Leu Ser Trp Pro Arg Glu Ile Pro
210                 215                 220

TTA GTA AAA GGT GGT AAA CCT GAC GTT GTA CAA ATT GTT AGG AAT TAT        720
Leu Val Lys Gly Gly Lys Pro Asp Val Val Gln Ile Val Arg Asn Tyr
225                 230                 235                 240

AAT GCT TAT CTA CGT GCA AGT GAT GAT TTA CCA AAA ATG TTT ATT GAA        768
Asn Ala Tyr Leu Arg Ala Ser Asp Asp Leu Pro Lys Met Phe Ile Glu
                245                 250                 255

TCG GAT CCA GGA TTC TTT TCC AAT GCT ATT GTT GAA GGC GCC AAG AAG        816
Ser Asp Pro Gly Phe Phe Ser Asn Ala Ile Val Glu Gly Ala Lys Lys
                260                 265                 270

TTT CCT AAT ACT GAA TTT GTC AAA GTA AAA GGT CTT CAT TTT TCG CAA        864
Phe Pro Asn Thr Glu Phe Val Lys Val Lys Gly Leu His Phe Ser Gln
            275                 280                 285

GAA GAT GCA CCT GAT GAA ATG GGA AAA TAT ATC AAA TCG TTC GTT GAG        912
Glu Asp Ala Pro Asp Glu Met Gly Lys Tyr Ile Lys Ser Phe Val Glu
290                 295                 300

CGA GTT CTC AAA AAT GAA CAA GCG GCC GCC GCC ACC ATG AGC AAG GGC        960
Arg Val Leu Lys Asn Glu Gln Ala Ala Ala Thr Met Ser Lys Gly
305                 310                 315                 320

GAG GAA CTG TTC ACT GGC GTG GTC CCA ATT CTC GTG GAA CTG GAT GGC       1008
Glu Glu Leu Phe Thr Gly Val Val Pro Ile Leu Val Glu Leu Asp Gly
                325                 330                 335

GAT GTG AAT GGG CAC AAA TTT TCT GTC AGC GGA GAG GGT GAA GGT GAT       1056
Asp Val Asn Gly His Lys Phe Ser Val Ser Gly Glu Gly Glu Gly Asp
                340                 345                 350

GCC ACA TAC GGA AAG CTC ACC CTG AAA TTC ATC TGC ACC ACT GGA AAG       1104
Ala Thr Tyr Gly Lys Leu Thr Leu Lys Phe Ile Cys Thr Thr Gly Lys
            355                 360                 365

CTC CCT GTG CCA TGG CCA ACA CTG GTC ACT ACC TTC ACC TAT GGC GTG       1152
Leu Pro Val Pro Trp Pro Thr Leu Val Thr Thr Phe Thr Tyr Gly Val
370                 375                 380

CAG TGC TTT TCC AGA TAC CCA GAC CAT ATG AAG CAG CAT GAC TTT TTC       1200
Gln Cys Phe Ser Arg Tyr Pro Asp His Met Lys Gln His Asp Phe Phe
385                 390                 395                 400

AAG AGC GCC ATG CCC GAG GGC TAT GTG CAG GAG AGA ACC ATC TTT TTC       1248
Lys Ser Ala Met Pro Glu Gly Tyr Val Gln Glu Arg Thr Ile Phe Phe
                405                 410                 415
```

```
AAA GAT GAC GGG AAC TAC AAG ACC CGC GCT GAA GTC AAG TTC GAA GGT          1296
Lys Asp Asp Gly Asn Tyr Lys Thr Arg Ala Glu Val Lys Phe Glu Gly
            420                 425                 430

GAC ACC CTG GTG AAT AGA ATC GAG CTG AAG GGC ATT GAC TTT AAG GAG          1344
Asp Thr Leu Val Asn Arg Ile Glu Leu Lys Gly Ile Asp Phe Lys Glu
            435                 440                 445

GAT GGA AAC ATT CTC GGC CAC AAG CTG GAA TAC AAC TAT AAC TCC CAC          1392
Asp Gly Asn Ile Leu Gly His Lys Leu Glu Tyr Asn Tyr Asn Ser His
        450                 455                 460

AAT GTG TAC ATC ATG GCC GAC AAG CAA AAG AAT GGC ATC AAG GTC AAC          1440
Asn Val Tyr Ile Met Ala Asp Lys Gln Lys Asn Gly Ile Lys Val Asn
465                 470                 475                 480

TTC AAG ATC AGA CAC AAC ATT GAG GAT GGA TCC GTG CAG CTG GCC GAC          1488
Phe Lys Ile Arg His Asn Ile Glu Asp Gly Ser Val Gln Leu Ala Asp
                485                 490                 495

CAT TAT CAA CAG AAC ACT CCA ATC GGC GAC GGC CCT GTG CTC CTC CCA          1536
His Tyr Gln Gln Asn Thr Pro Ile Gly Asp Gly Pro Val Leu Leu Pro
            500                 505                 510

GAC AAC CAT TAC CTG TCC ACC CAG TCT GCC CTG TCT AAA GAT CCC ACC          1584
Asp Asn His Tyr Leu Ser Thr Gln Ser Ala Leu Ser Lys Asp Pro Asn
            515                 520                 525

GAA AAG AGA GAC CAC ATG GTC CTG CTG GAG TTT GTG ACC GCT GCT GGG          1632
Glu Lys Arg Asp His Met Val Leu Leu Glu Phe Val Thr Ala Ala Gly
        530                 535                 540

ATC ACA CAT GGC ATG GAC GAG CTG TAC AAG TGA                              1665
Ile Thr His Gly Met Asp Glu Leu Tyr Lys
545                 550

(2) INFORMATION FOR SEQ ID NO:2:

(i) SEQUENCE CHARACTERISTICS:
        (A) LENGTH: 1677 base pairs
        (B) TYPE: nucleic acid
        (C) STRANDEDNESS: single
        (D) TOPOLOGY: linear (xi) SEQUENCE DESCRIPTION: SEQ ID NO:2:

ATG AGC AAG GGC GAG GAA CTG TTC ACT GGC GTG GTC CCA ATT CTC GTG           48
Met Ser Lys Gly Glu Glu Leu Phe Thr Gly Val Val Pro Ile Leu Val
1               5                   10                  15

GAA CTG GAT GGC GAT GTG AAT GGG CAC AAA TTT TCT GTC AGC GGA GAG           96
Glu Leu Asp Gly Asp Val Asn Gly His Lys Phe Ser Val Ser Gly Glu
            20                  25                  30

GGT GAA GGT GAT GCC ACA TAC GGA AAG CTC ACC CTG AAA TTC ATC TGC          144
Gly Glu Gly Asp Ala Thr Tyr Gly Lys Leu Thr Leu Lys Phe Ile Cys
        35                  40                  45

ACC ACT GGA AAG CTC CCT GTG CCA TGG CCA ACA CTG GTC ACT ACC TTC          192
Thr Thr Gly Lys Leu Pro Val Pro Trp Pro Thr Leu Val Thr Thr Phe
    50                  55                  60

ACC TAT GGC GTG CAG TGC TTT TCC AGA TAC CCA GAC CAT ATG AAG CAG          240
Thr Tyr Gly Val Gln Cys Phe Ser Arg Tyr Pro Asp His Met Lys Gln
65                  70                  75                  80

CAT GAC TTT TTC AAG AGC GCC ATG CCC GAG GGC TAT GTG CAG GAG AGA          288
His Asp Phe Phe Lys Ser Ala Met Pro Glu Gly Tyr Val Gln Glu Arg
                85                  90                  95

ACC ATC TTT TTC AAA GAT GAC GGG AAC TAC AAG ACC CGC GCT GAA GTC          336
Thr Ile Phe Phe Lys Asp Asp Gly Asn Tyr Lys Thr Arg Ala Glu Val
            100                 105                 110

AAG TTC GAA GGT GAC ACC CTG GTG AAT AGA ATC GAG CTG AAG GGC ATT          384
Lys Phe Glu Gly Asp Thr Leu Val Asn Arg Ile Glu Leu Lys Gly Ile
        115                 120                 125
```

-continued

| | | | | | | | | | | | | | | | | |
|---|---|---|---|---|---|---|---|---|---|---|---|---|---|---|---|---|
| GAC | TTT | AAG | GAG | GAT | GGA | AAC | ATT | CTC | GGC | CAC | AAG | CTG | GAA | TAC | AAC | 432 |
| Asp | Phe | Lys | Glu | Asp | Gly | Asn | Ile | Leu | Gly | His | Lys | Leu | Glu | Tyr | Asn | |
| | 130 | | | | 135 | | | | | 140 | | | | | | |

| | | | | | | | | | | | | | | | | |
|---|---|---|---|---|---|---|---|---|---|---|---|---|---|---|---|---|
| TAT | AAC | TCC | CAC | AAT | GTG | TAC | ATC | ATG | GCC | GAC | AAG | CAA | AAG | AAT | GGC | 480 |
| Tyr | Asn | Ser | His | Asn | Val | Tyr | Ile | Met | Ala | Asp | Lys | Gln | Lys | Asn | Gly | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ATC | AAG | GTC | AAC | TTC | AAG | ATC | AGA | CAC | AAC | ATT | GAG | GAT | GGA | TCC | GTG | 528 |
| Ile | Lys | Val | Asn | Phe | Lys | Ile | Arg | His | Asn | Ile | Glu | Asp | Gly | Ser | Val | |
| | | | | 165 | | | | | 170 | | | | | 175 | | |

| | | | | | | | | | | | | | | | | |
|---|---|---|---|---|---|---|---|---|---|---|---|---|---|---|---|---|
| CAG | CTG | GCC | GAC | CAT | TAT | CAA | CAG | AAC | ACT | CCA | ATC | GGC | GAC | GGC | CCT | 576 |
| Gln | Leu | Ala | Asp | His | Tyr | Gln | Gln | Asn | Thr | Pro | Ile | Gly | Asp | Gly | Pro | |
| | | | 180 | | | | | 185 | | | | | 190 | | | |

| | | | | | | | | | | | | | | | | |
|---|---|---|---|---|---|---|---|---|---|---|---|---|---|---|---|---|
| GTG | CTC | CTC | CCA | GAC | AAC | CAT | TAC | CTG | TCC | ACC | CAG | TCT | GCC | CTG | TCT | 624 |
| Val | Leu | Leu | Pro | Asp | Asn | His | Tyr | Leu | Ser | Thr | Gln | Ser | Ala | Leu | Ser | |
| | | 195 | | | | | 200 | | | | | 205 | | | | |

| | | | | | | | | | | | | | | | | |
|---|---|---|---|---|---|---|---|---|---|---|---|---|---|---|---|---|
| AAA | GAT | CCC | AAC | GAA | AAG | AGA | GAC | CAC | ATG | GTC | CTG | CTG | GAG | TTT | GTG | 672 |
| Lys | Asp | Pro | Asn | Glu | Lys | Arg | Asp | His | Met | Val | Leu | Leu | Glu | Phe | Val | |
| 210 | | | | | 215 | | | | | 220 | | | | | | |

| | | | | | | | | | | | | | | | | |
|---|---|---|---|---|---|---|---|---|---|---|---|---|---|---|---|---|
| ACC | GCT | GCT | GGG | ATC | ACA | CAT | GGC | ATG | GAC | GAG | CTG | TAC | AAG | GGG | TAC | 720 |
| Thr | Ala | Ala | Gly | Ile | Thr | His | Gly | Met | Asp | Glu | Leu | Tyr | Lys | Gly | Tyr | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| CAG | ATC | GAA | TTC | AGC | TTA | AAG | ATG | ACT | TCG | AAA | GTT | TAT | GAT | CCA | GAA | 768 |
| Gln | Ile | Glu | Phe | Ser | Leu | Lys | Met | Thr | Ser | Lys | Val | Tyr | Asp | Pro | Glu | |
| | | | | 245 | | | | | 250 | | | | | 255 | | |

| | | | | | | | | | | | | | | | | |
|---|---|---|---|---|---|---|---|---|---|---|---|---|---|---|---|---|
| CAA | AGG | AAA | CGG | ATG | ATA | ACT | GGT | CCG | CAG | TGG | TGG | GCC | AGA | TGT | AAA | 816 |
| Gln | Arg | Lys | Arg | Met | Ile | Thr | Gly | Pro | Gln | Trp | Trp | Ala | Arg | Cys | Lys | |
| | | | 260 | | | | | 265 | | | | | 270 | | | |

| | | | | | | | | | | | | | | | | |
|---|---|---|---|---|---|---|---|---|---|---|---|---|---|---|---|---|
| CAA | ATG | AAT | GTT | CTT | GAT | TCA | TTT | ATT | AAT | TAT | TAT | GAT | TCA | GAA | AAA | 864 |
| Gln | Met | Asn | Val | Leu | Asp | Ser | Phe | Ile | Asn | Tyr | Tyr | Asp | Ser | Glu | Lys | |
| | | 275 | | | | | 280 | | | | | 285 | | | | |

| | | | | | | | | | | | | | | | | |
|---|---|---|---|---|---|---|---|---|---|---|---|---|---|---|---|---|
| CAT | GCA | GAA | AAT | GCT | GTT | ATT | TTT | TTA | CAT | GGT | AAC | GCG | GCC | TCT | TCT | 912 |
| His | Ala | Glu | Asn | Ala | Val | Ile | Phe | Leu | His | Gly | Asn | Ala | Ala | Ser | Ser | |
| 290 | | | | | 295 | | | | | 300 | | | | | | |

| | | | | | | | | | | | | | | | | |
|---|---|---|---|---|---|---|---|---|---|---|---|---|---|---|---|---|
| TAT | TTA | TGG | CGA | CAT | GTT | GTG | CCA | CAT | ATT | GAG | CCA | GTA | GCG | CGG | TGT | 960 |
| Tyr | Leu | Trp | Arg | His | Val | Val | Pro | His | Ile | Glu | Pro | Val | Ala | Arg | Cys | |
| 305 | | | | | 310 | | | | | 315 | | | | | 320 | |

| | | | | | | | | | | | | | | | | |
|---|---|---|---|---|---|---|---|---|---|---|---|---|---|---|---|---|
| ATT | ATA | CCA | GAT | CTT | ATT | GGT | ATG | GGC | AAA | TCA | GGC | AAA | TCT | GGT | AAT | 1008 |
| Ile | Ile | Pro | Asp | Leu | Ile | Gly | Met | Gly | Lys | Ser | Gly | Lys | Ser | Gly | Asn | |
| | | | | 325 | | | | | 330 | | | | | 335 | | |

| | | | | | | | | | | | | | | | | |
|---|---|---|---|---|---|---|---|---|---|---|---|---|---|---|---|---|
| GGT | TCT | TAT | AGG | TTA | CTT | GAT | CAT | TAC | AAA | TAT | CTT | ACT | GCA | TGG | TTT | 1056 |
| Gly | Ser | Tyr | Arg | Leu | Leu | Asp | His | Tyr | Lys | Tyr | Leu | Thr | Ala | Trp | Phe | |
| | | | 340 | | | | | 345 | | | | | 350 | | | |

| | | | | | | | | | | | | | | | | |
|---|---|---|---|---|---|---|---|---|---|---|---|---|---|---|---|---|
| GAA | CTT | CTT | AAT | TTA | CCA | AAG | AAG | ATC | ATT | TTT | GTC | GGC | CAT | GAT | TGG | 1104 |
| Glu | Leu | Leu | Asn | Leu | Pro | Lys | Lys | Ile | Ile | Phe | Val | Gly | His | Asp | Trp | |
| | | 355 | | | | | 360 | | | | | 365 | | | | |

| | | | | | | | | | | | | | | | | |
|---|---|---|---|---|---|---|---|---|---|---|---|---|---|---|---|---|
| GGT | GCT | TGT | TTG | GCA | TTT | CAT | TAT | AGC | TAT | GAG | CAT | CAA | GAT | AAG | ATC | 1152 |
| Gly | Ala | Cys | Leu | Ala | Phe | His | Tyr | Ser | Tyr | Glu | His | Gln | Asp | Lys | Ile | |
| | 370 | | | | | 375 | | | | | 380 | | | | | |

| | | | | | | | | | | | | | | | | |
|---|---|---|---|---|---|---|---|---|---|---|---|---|---|---|---|---|
| AAA | GCA | ATA | GTT | CAC | GCT | GAA | AGT | GTA | GTA | GAT | GTG | ATT | GAA | TCA | TGG | 1200 |
| Lys | Ala | Ile | Val | His | Ala | Glu | Ser | Val | Val | Asp | Val | Ile | Glu | Ser | Trp | |
| 385 | | | | | 390 | | | | | 395 | | | | | 400 | |

| | | | | | | | | | | | | | | | | |
|---|---|---|---|---|---|---|---|---|---|---|---|---|---|---|---|---|
| GAT | GAA | TGG | CCT | GAT | ATT | GAA | GAA | GAT | ATT | GCG | TTG | ATC | AAA | TCT | GAA | 1248 |
| Asp | Glu | Trp | Pro | Asp | Ile | Glu | Glu | Asp | Ile | Ala | Leu | Ile | Lys | Ser | Glu | |
| | | | | 405 | | | | | 410 | | | | | 415 | | |

| | | | | | | | | | | | | | | | | |
|---|---|---|---|---|---|---|---|---|---|---|---|---|---|---|---|---|
| GAA | GGA | GAA | AAA | ATG | GTT | TTG | GAG | AAT | AAC | TTC | TTC | GTG | GAA | ACC | ATG | 1296 |
| Glu | Gly | Glu | Lys | Met | Val | Leu | Glu | Asn | Asn | Phe | Phe | Val | Glu | Thr | Met | |
| | | | 420 | | | | | 425 | | | | | 430 | | | |

| | | | | | | | | | | | | | | | | |
|---|---|---|---|---|---|---|---|---|---|---|---|---|---|---|---|---|
| TTG | CCA | TCA | AAA | ATC | ATG | AGA | AAG | TTA | GAA | CCA | GAA | GAA | TTT | GCA | GCA | 1344 |
| Leu | Pro | Ser | Lys | Ile | Met | Arg | Lys | Leu | Glu | Pro | Glu | Glu | Phe | Ala | Ala | |
| | | 435 | | | | | 440 | | | | | 445 | | | | |

-continued

```
TAT CTT GAA CCA TTC AAA GAG AAA GGT GAA GTT CGT CGT CCA ACA TTA          1392
Tyr Leu Glu Pro Phe Lys Glu Lys Gly Glu Val Arg Arg Pro Thr Leu
    450                 455                 460

TCA TGG CCT CGT GAA ATC CCG TTA GTA AAA GGT GGT AAA CCT GAC GTT          1440
Ser Trp Pro Arg Glu Ile Pro Leu Val Lys Gly Gly Lys Pro Asp Val
465                 470                 475                 480

GTA CAA ATT GTT AGG AAT TAT AAT GCT TAT CTA CGT GCA AGT GAT GAT          1488
Val Gln Ile Val Arg Asn Tyr Asn Ala Tyr Leu Arg Ala Ser Asp Asp
                485                 490                 495

TTA CCA AAA ATG TTT ATT GAA TCG GAT CCA GGA TTG TTT TCC AAT GCT          1536
Leu Pro Lys Met Phe Ile Glu Ser Asp Pro Gly Leu Phe Ser Asn Ala
        500                 505                 510

ATT GTT GAA GGC GCC AAG AAG TTT CCT AAT ACT GAA TTT GTC AAA GTA          1584
Ile Val Glu Gly Ala Lys Lys Phe Pro Asn Thr Glu Phe Val Lys Val
    515                 520                 525

AAA GGT CTT CAT TTT TCG CAA GAA GAT GCA CCT GAT GAA ATG GGA AAA          1632
Lys Gly Leu His Phe Ser Gln Glu Asp Ala Pro Asp Glu Met Gly Lys
530                 535                 540

TAT ATC AAA TCG TTC GTT GAG CGA GTT CTC AAA AAT GAA CAA TAA              1677
Tyr Ile Lys Ser Phe Val Glu Arg Val Leu Lys Asn Glu Gln
545                 550                 555
```

(2) INFORMATION FOR SEQ ID NO:3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear     (xi) SEQUENCE DESCRIPTION: SEQ ID NO:3:

CTGCAGAGGA GGAATTCAGC TTAAAGATG          29

(2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear     (xi) SEQUENCE DESCRIPTION:SEQ ID NO:4:

GCGGCCGCTT GTTCATTTTT GAGAAC          26

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear     (xi) SEQUENCE DESCRIPTION:SEQ ID NO:5:

GGGGTACCCC ATGAGCAAGG GCGAGGAACT          30

(2) INFORMATION FOR SEQ ID NO:6:

(i) SEQUENCE CHARACTERISTICS:
        (A) LENGTH: 31 base pairs
        (B) TYPE: nucleic acid
        (C) STRANDEDNESS: single
        (D) TOPOLOGY: linear     (xi) SEQUENCE DESCRIPTION:SEQ ID NO:6:

GGGGTACCCC TTGTACAGCT CGTCCATGCC A          31

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear     (xi) SEQUENCE DESCRIPTION:SEQ ID NO:7:

CCCGGGAGGA GGTACCCCAT GAGCAAG                            27